(12) United States Patent
Li et al.

(10) Patent No.: US 6,716,225 B2
(45) Date of Patent: Apr. 6, 2004

(54) IMPLANT DEVICES FOR NERVE REPAIR

(75) Inventors: Shu-Tung Li, Oakland, NJ (US);
Debbie Yuen, Woodcliff Lake, NJ (US)

(73) Assignee: Collagen Matrix, Inc., Franklin Lakes, NJ (US)

( * ) Notice: Subject to any disclaimer, the term of this patent is extended or adjusted under 35 U.S.C. 154(b) by 0 days.

(21) Appl. No.: 09/921,146

(22) Filed: Aug. 2, 2001

(65) Prior Publication Data

US 2003/0028204 A1 Feb. 6, 2003

(51) Int. Cl.$^7$ ................................................ A61B 17/08
(52) U.S. Cl. ........................ 606/152; 623/1.38; 600/36
(58) Field of Search ........................... 606/76, 77, 152; 623/1.38, 1.39, 1.4, 1.41, 1.47, 1.54, 921; 264/86; 600/36

(56) References Cited

U.S. PATENT DOCUMENTS

| | | | | |
|---|---|---|---|---|
| 4,252,759 A | * | 2/1981 | Yannas et al. ................ | 264/86 |
| 4,534,349 A | * | 8/1985 | Barrows ..................... | 606/152 |
| 4,787,900 A | * | 11/1988 | Yannas ...................... | 623/921 |
| 4,877,029 A | * | 10/1989 | Valentini et al. ............ | 606/152 |
| 4,963,146 A | * | 10/1990 | Li ............................ | 606/152 |
| 5,026,381 A | | 6/1991 | Li | |
| 5,834,029 A | * | 11/1998 | Bellamkonda et al. ...... | 606/152 |

OTHER PUBLICATIONS

Kline et al., "The Use of a Resorable Wrapper for Peripheral-Nerve Repair," Journal of Neurosurgery (1964) vol. XXI, No. 9, pps. 737–750.

Colin et al., "Nerve Regeneration Through Collagen Tubes," J. Dent. Res. (Jul. 1984) vol. 63, No. 7, pps. 987–993.

"Latest Advances in Adrenal Gland Transplants to Treat Parkinsonism, " Progress in Research, issue 18 (Fall 1987).

Eppley et al., "Collagen Tube Repair of the Mandibular Nerve: A Preliminary Investigation in the Rat," J. Oral Maxillofac. Surg., 46:41–47 (1988).

Vascutek Triaxial.

Kim et al., "Interposition of Sural Nerve Restores Function of Cavernous Nerves Resected During Radical Prostatectomy," The Journal of Urology, vol. 161, 188–192 (Jan. 1999).

Archibald et a;., "A Collagen–Based Nerve Guide Conduit for Peripheral Nerve Repair: An Electrophysiological Study of Nerve Regeneration in Rodents and Nonhuman Primates," The Journal of Comparative Neurology, 306:685–696 (1991).

King et al., "Designing Polyester Vascular Prostheses for the Future," Med. Progr. Technol., 9,217–226 (1983).

* cited by examiner

Primary Examiner—Julian W. Woo
(74) Attorney, Agent, or Firm—Fish & Richardson P.C.

(57) ABSTRACT

An implant device including a tubular matrix made of a biocompatible and bioresorbable biopolymeric material. The matrix has a first end and a second end, a wall of a homogeneous thickness; a plurality of ridges on the wall; and a channel which is defined by the wall and extends from the first end to the second end of the tubular matrix.

54 Claims, 1 Drawing Sheet

IMPLANT DEVICES FOR NERVE REPAIR

BACKGROUND OF THE INVENTION

Damage to a peripheral nerve makes acts of daily life very inconvenient, if not impossible. For example, injury to the cavernosal nerve results in impotency.

A challenge in nerve repair is to restore continuity between the proximal and distal nerve stumps. When there is a nerve gap distance that must be bridged, it may be impossible to bring the cut nerve stumps into proximity close enough to achieve a direct suture repair. In this case, a certain type of intervening material must be used. The most commonly used material is an autograft of a peripheral nerve harvested from the patient, e.g., a sural nerve autograft. The surgical repair procedure is tedious and time-consuming. However, there is no alternative to the autograft at this time.

Therefore, it would be desirable to have an alternative nerve graft material that not only fulfills the requirements, but also overcomes many of the shortcomings, of a nerve autograft. Indeed, many types of biomaterials, natural or synthetic, have been used to make tubes or conduits for guiding peripheral nerve regeneration. Although this technology, which is commonly called "entubulation repair," has several theoretical advantages over nerve autografting, the results still are not satisfactory for repairing long nerve defects.

The tubes or conduits for guiding peripheral nerve regeneration are commonly made of materials such as polylactide, polylactide/polyglycolide copolymers, acrylic copolymers, polyvinylidene fluoride, polyglactin mesh, Millipore filter material, silicone, GORE-TEX® (expanded polytetrafluoroethylene), arterial cuffs, preformed mesothelial tubes or various other synthetic polyesters. The shortcomings of using a tube or conduit made of these materials include immune responses, induction of scar tissue, difficulty in application, and development of local elevated concentrations of compounds released after the degradation of a degradable material used in the device. For a tube or conduit made of non-degradable materials, e.g., polyvinylidene fluoride, a second surgery is often necessary for removal of the tube or conduit.

Further, although these devices are tubular, they do not all provide kink resistance. Kink resistance (i.e., resistance to forming a crease or a sharp bending of the wall) is particularly important in cases which require bending of the device for proper connections, such as nerve repairs in wrists and hands. Kinking of a nerve-guiding tube causes nerve compression and potential axonal disruption and neuroma formation.

In addition, certain devices are not effective to bridge a long gap distance, e.g. 2 cm or longer. Typically, their use results in a regenerated nerve cable that is thinner than desirable.

Further, the in vivo stability of certain implant devices for nerve repair is not clear. Thus, the utility of such implant devices is questionable in that they may prematurely fail and thus be unsuitable for methods involving longer gap nerve regeneration (e.g. longer than 2 cm).

Therefore, there is a need for a biocompatible, resorbable, semipermeable, and kink resistant tubular implant for nerve repair.

SUMMARY OF THE INVENTION

The present invention pertains to an implant device made of a biocompatible, bioresorbable, and biopolymeric material.

More specifically, the present invention relates to an implant device including a tubular matrix. The tubular matrix has a first end and a second end, a wall of a uniform thickness and disposed such that it forms ridges, and a channel which is defined by the wall of the matrix and extends from the first end to the second end of the matrix. The implant device can be utilized for tissue repair, including nerve repair, vascular repair, urological tissue repair, esophageal repair, and intestinal tissue repair.

One subset of the implant devices of this invention further include a plurality of cylindrical matrices made of a biocompatible and bioresorbable biopolymeric material. The cylindrical matrices are disposed inside the channel and parallel to the longitudinal axis of the tubular matrix. Each cylindrical matrix has two ends, a wall of a uniform thickness and disposed such that it forms a plurality of ridges, and a passage which is defined by its wall and extends from one end to the other end of the cylindrical matrix. One passage, or alternatively a plurality of passages, of a cylindrical matrix is of suitable dimension for receiving the nerve to be repaired. For example, the longitudinal passage dimension can be about 40–99% (e.g., about 40–95%, about 80–95%, about 60–95%, about 70–90%, about 50–90%, about 85–99%) of the dimension of the tubular matrix. The passage can alternatively be between about 0.01 mm and 1.0 mm in width. In one embodiment, the tubular matrix has an internal diameter of about 0.1 mm to 10 mm, a length of about 0.3 cm to 15 cm, and a thickness of about 0.02 mm to 1 mm; and each cylindrical matrix has an internal diameter of about 0.1 mm to 2 mm, a length of about 0.3 cm to 15 cm, and a thickness of about 0.02 mm to 1.0 mm; or alternatively an internal diameter of about 0.1 mm to 2 mm, a length of about 0.3 cm to 15 cm, and a thickness of about 0.02 mm to 0.5 mm.

Another subset of the implant devices of this invention further include a plurality of filaments made of a biocompatible and bioresorbable biopolymeric material, wherein the filaments are disposed inside the channel and parallel to the longitudinal axis of the tubular matrix, thereby forming inter-filamental spaces which extend along the tubular matrix; and at least one inter-filamental space is dimensioned for receiving the nerve to be repaired. For example, the filament length can be about 40–95% of the length of the tubular matrix. The inter-filamental space can alternatively be between about 0.01 mm and 1.0 mm in width. In one embodiment, the tubular matrix has an internal diameter of about 0.1 mm to 10 mm, a length of about 0.3 cm to 15 cm, and a thickness of about 0.02 mm to 1 mm; and each filament has a diameter of about 0.03 mm to 0.5 mm and a length of about 0.3 cm to 15 cm.

Still another subset of the implant devices of this invention further include one or more porous cylindrical matrices made of a biocompatible and bioresorbable biopolymeric material. A porous matrix refers to a solid material that contains pores. The pore size for the porous matrix can be from about 10 $\mu$m to about 800 $\mu$m, alternatively it can be from about 10 $\mu$m to about 500 $\mu$m, alternatively from about 20 $\mu$m to about 300 $\mu$m. The porous cylindrical matrices are disposed inside the channel of the tubular matrix and parallel to the tubular matrix. Each porous cylindrical matrix has two ends and at least one passage which is parallel to its longitudinal axis and extending from one end to the other end of the porous cylindrical matrix. One passage of a porous cylindrical matrix is of suitable dimension for receiving the nerve to be repaired. For example, the porous cylindrical matrix length can be about 40–95% of the length of the tubular matrix. The passage can alternatively be between about 0.01 mm and 1.0 mm in width. In one embodiment, the tubular matrix has an internal diameter of about 0.1 mm to 10 mm, a length of about 0.3 cm to 15 cm, and a thickness of about 0.02 mm to 1 mm; each porous cylindrical matrix has a diameter of about 0.1 mm to 10 mm and a length of about 0.3 cm to 15 cm; and each passage of each porous cylindrical matrix has a diameter of about 0.1 mm to 2 mm and a length of about 0.3 cm to 15 cm; alternatively each porous cylindrical matrix has a diameter of about 1 mm to 5 mm.

The invention also relates to a method of preparing a ridged tubular matrix. The method includes the following steps: fabricating a tubular matrix comprising biopolymeric fibers; drying the tubular matrix; humidifying the tubular matrix; pressing the tubular matrix along its longitudinal axis to cause formation of ridges on the wall thereof; and crosslinking the biopolymeric fibers to obtain a ridged tubular matrix. In an alternate aspect, the method may comprise a ridge formation step including fabricating the fibers using a ridged mandrel, in place of the pressing of the tubular matrix step to cause ridge formation. The term "fabricating" refers to any method of manufacturing the matrix with or without the aid of an instrument.

In another embodiment, the implant device (e.g., tubular matrix) has an internal diameter of about 1 mm to 5 mm, alternatively about 1 mm to 4.5 mm, alternatively about 1 mm to 4 mm, alternatively about 1 mm to 3 mm, in combination with any of the length and thickness dimensions delineated herein.

In another embodiment, the implant device (e.g., tubular matrix) has a length of about 0.3 cm to 15 cm, alternatively about 0.3 cm to 10 cm, alternatively about 0.3 cm to 5 cm in combination with any of the diameter and thickness dimensions delineated herein.

In one embodiment, the implant device of the invention has a length from about 1 cm to 15 cm, internal diameter from about 1 mm to 10 mm and thickness from about 0.2 mm to 1 mm, alternatively it has an internal diameter of about 0.1 mm to 10 mm, a length of about 0.3 cm to 15 cm, and a thickness of about 0.02 mm to 1 mm.

The details of several embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
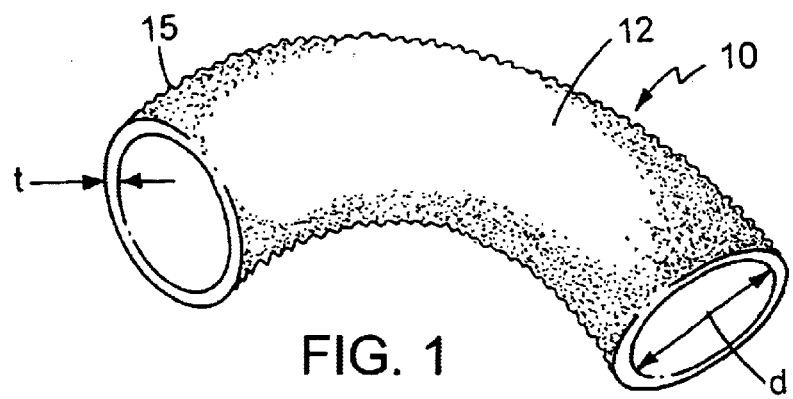
FIG. 1 is a perspective view of an implant device of this invention. The bending of the tubular implant device demonstrates the kink-resistance of the implant device.
Figure 2:
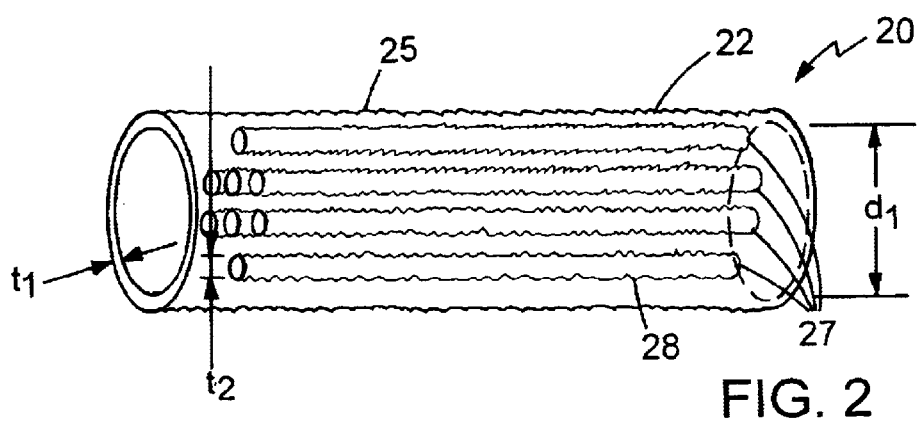
FIG. 2 is a perspective view of an implant device of this invention with a micro guiding system. The micro guiding system is defined by the walls of micro-tubes.
Figure 3:
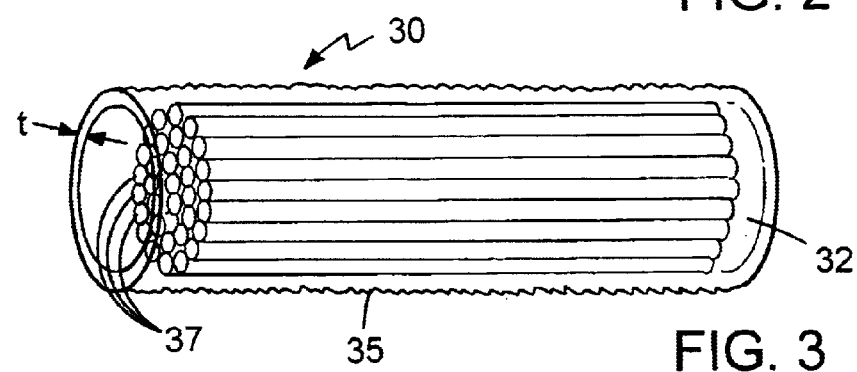
FIG. 3 is a perspective view of an implant device of this invention with a micro guiding system. The micro guiding system is the inter-filamental space.
Figure 4:
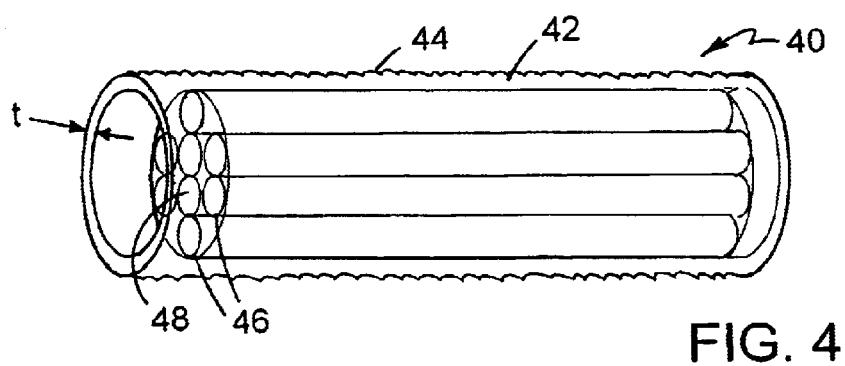
FIG. 4 is a kink resistant tubular implant device of this invention with a micro guiding system. The micro guiding system is the channels in the porous matrices.

The present invention relates to an implant device including a tubular matrix. The tubular matrix has a first end and a second end, a wall of a uniform thickness and disposed such that it forms ridges, and a channel which is defined by the wall of the matrix and is extending from the first end to the second end of the tubular matrix. See FIG. 1. The implant device optionally includes microtubes, filaments, or porous matrices, which are disposed (e.g., inserted in parallel, inserted longitudinally, or inserted randomly) in the channel of the device and define a micro guiding system which can improve cell adhesion and guide cell migration for bridging longer gaps. See FIG. 2, 3, or 4. The elements (e.g., microtubes, filaments, or porous matrices) are essentially parallel, or considered parallel, if the angle formed by a line perpendicular to one element and the angle formed by the same line and the other element are within 25%, alternatively 10%, alternatively 5%, of one another. More specifically, such a micro-guiding system includes the channels of the microtubes, the inter-filamentary space, or the channels within the porous matrices. The implant device is biodegradable and bioresorbable, semipermeable, and kink-resistant. It is suitable for nerve repair, vascular repair, urological tissue repair, esophagus repair, and intestinal tissue repair.

The tubular matrix, microtubes, filaments, or porous matrices mentioned above, are made of a biocompatible and bioresorbable biopolymeric material. A biocompatible material is a material that is of specific strength, permeability, durability, etc., and is able to perform in a specific application within a host without causing undesirable biological reactions such as an acute inflammatory reaction. Strength refers to the ability of resisting force, strain, or stress; permeability refers to the condition of being permeable to molecules of certain molecular weights, and durability refers to ability to continue to function over an extended period of time. A bioresorbable material is one that can degrade, e.g., by proteolysis, to lower molecular weight fragments which can be used by the host or are readily removed and or further degraded by the host. Examples of such biocompatible and bioresorbable materials include various types of collagens, polysaccharides, other proteins including fibrin or elastin, and collagen-based materials (i.e., a material that includes or is derived from collagen) such as a collagen-heparin composite, a collagen-growth factor composite and a collagen-cell composite. A host can be a subject (e.g., human, animal, including dog, cat, horse, cow, bird, fish, or reptile) in which the implant device is implanted.

The ridges in the outer wall surface of the device are illustrated in FIGS. 1–4. These ridges result in the appearance of uniform serrations or undulations in the surface. The ridges are generally uniform in size, and are generally uniform in circumference around the outer wall surface of the device, that is the circumference around each peak of a ridge is generally uniform with other peaks and the circumference around each valley of a ridge is generally uniform with other valleys. In one aspect, the physical size (e.g., diameter, circumference, elevation, thickness, length, width, or height) of the ridges of the device is generally similar, that is within a certain percentage (e.g., 50%, 30%, 20%, 15%, 10%, or 5%) of the size of all other ridges in the device. Such ridges can, for example, be created by compression of the device during fabrication, (e.g., in a longitudinal direction on a tubular shaped device) or by fabricating onto a ridged mandrel. The wall of the devices of the invention can have a uniform thickness, that is, the wall thickness at any point (e.g., a first comparison point) in the device is within a certain percentage (e.g., 50%, 30%, 20%, 15%, 10%, or 5%) of the thickness of the same wall at any other point (e.g., a second comparison point) in the device. In one aspect, the comparison points must be similar, that is, a ridge peak is to be compared with a ridge peak and a ridge valley is to be compared to a ridge valley for purposes of evaluating thickness. In another aspect, the wall is of uniform thickness throughout the entire device, that is, at any two comparison points in the wall of the device. The ridges of the device provide flexibility in the device such that the device can withstand manipulation (e.g., folding, bending, twisting, or turning) necessary for nerve connection purposes, yet, resists kinking (e.g., creasing or sharp bending) such that nerve compression results, or that fractures in the wall of the device occur.

The pore size for the porous matrix can also be characterized in terms of permeability of the membrane (e.g., in cases when the pore are compressed to what effectively are linear sheet layers). Permeability is a direct measure of how permeable a membrane (e.g., porous matrix) is to macromolecules of a defined molecular weight. For example, if the membrane is permeable to a 30,000 daltons macromolecule, then the equivalent pore size is about 40 Å (assuming that molecules in solution are in globular form).

The tubular matrix can have a molecular weight cutoff (MWCO) of about 500,000, alternatively about 200,000, alternatively about 100,000, alternatively about 50,000 or alternatively about 30,000. The MWCO refers to the molecular weight at which the membrane effectively distinguishes molecules. When a molecule or an object (e.g., particle, cell) has a molecular weight (or an equivalent size) higher (or larger) than the MWCO of a membrane, the molecule or object will be retained on the surface of the membrane; while a molecule or an object of a molecular weight (or an equivalent size) lower (or smaller) than the MWCO is allowed to pass through the membrane.

The device can also include bioactive molecules, such as growth factors and bioadhesive molecules, to promote cell adhesion, growth, and differentiation. Suitable bioactive molecules include growth factors such as acidic and basic fibroblast growth factors, insulin-like growth factors, epidermal growth factors, bone morphogenetic proteins, nerve growth factors, neurotrophic factors, TGF-β, platelet derived growth factors, vascular endothelial cell growth factor, and the like that have the biological activity of mitogenesis or angiogenesis. Bioadhesive molecules useful for the invention include the family of laminins, family of fibronectins, adhesive glycoproteins, fibrin, glycosaminoglycans, various cell adhesive collagens, and the like that can promote cell adhesion and guide cell migration. The growth factors and adhesive molecules may be incorporated into the implant and micro guiding systems via physical and mechanical interactions, electrostatic interactions, and covalent interaction using a crosslinking agent or by dye-sensitive photo-oxidation. The device can also further include cells, which in part can aid in promoting biocompatibility, and growth and regeneration (e.g., nerve growth). A variety of cells are useful in the device (and uses thereof), including Schwann cells, endothelial cells, epithelial cells, Sertoli's cells, fibroblasts, stem cells, or any cells useful or desirable in applications for tissue or nerve repair.

Without further elaboration, it is believed that one skilled in the art can, based on the description herein, utilize the present invention to its fullest extent. All publications recited herein are hereby incorporated by reference in their entirety. The following examples, which describe representative methods of making and using implant devices of this invention, is therefore, to be construed as merely illustrative, and not limitative of the disclosure in any way.

EXAMPLE 1

Preparation of Collagen Fibers

Bovine flexor tendon is cleaned by removing fat and fascia, and washing with water. The cleaned tendon is frozen and comminuted into 0.5 mm slices with a meat slicer. One kilogram of the sliced wet tendon is subsequently extracted with 5 L of distilled water and with 5 L of 0.2 N HCl/0.5 M $Na_2SO_4$ solution at room temperature for 24 hours, the extracts are discarded. The residual acid on the tendon is removed by washing with 5 L of 0.5M $Na_2SO_4$ solution. The tendon is again extracted with 5 L of 0.75 M NaOH/1.0 M $Na_2SO_4$ solution at room temperature for 24 hours. The extract is also discarded. The residual base is neutralized with a 0.01N HCl solution to pH 5, followed by several washes with distilled water to remove the residual salts on the purified tendon. The tendon is then defatted at 25° C. under constant agitation with isopropanol of 5 times the volume of the tendon for 8 hours and an equal volume of the tendon overnight. The defatted tendon is then air-dried and stored at room temperature until further processing.

EXAMPLE 2

Preparation of Collagen Fiber Dispersion

An aliquot of the insoluble collagen fibers was weighed and dispersed in 0.07 M lactic acid, homogenized with a Silverson Homogenizer (East Longmeadow, Mass.), and filtered with a 30 mesh stainless steel mesh filter to obtain a dispersion containing 0.7% (w/v) collagen. The dispersion was de-aerated under vacuum to remove the air trapped in the dispersion and stored at 4° C. until use.

EXAMPLE 3

Preparation of a Tubular Implant Device

The acid dispersed collagen fibers prepared in Example 2 were reconstituted by adding 0.3% $NH_4OH$ to adjust the pH of the dispersion to the isoelectric point of collagen (pH 4.5–5.0). The reconstituted fibers were poured into a fabrication device which is set up with the insertion of a mandrel of 1 mm, 1.5 mm, 2 mm, 2.5 mm, 3.0 mm, 3.5 mm, 4 mm, 5 mm, 6 mm or 10 mm in diameter. The fibers were evenly distributed along the mandrel. The mandrel was then slowly rotated at about 40–50 rpm to firmly wind the fibers around it. The fibers on the mandrel were removed from the fabrication device and then inserted into a precision dehydration device for removal of excess solution and control of the thickness and density of the tubular wall. Dehydration of the device resulted in increased wall density of the device and decreased pore size (i.e., the inter-fiber space), thereby affecting the permeability of the wall. The excess solution was removed by compressing the hydrated fibers on the rotating mandrel against two plates that precisely control the thickness of the wall of the membrane.

The partially dehydrated collagen fibers were freeze-dried at −10° C. for 24 hours and at 20° C. for 16 hours under a pressure less than 200 millitorr using a Virtis Freeze Dryer (Gardiner, N.Y.). The freeze-dried tubular matrix was removed from the mandrel and reinserted into another mandrel having a diameter slightly smaller than the first mandrel to facilitate the ridge formation described below. The dried tubular matrix was humidified in an environment of 80–100% humidity for 1–8 hours. The humidified matrix was then slowly pushed at both ends along the longitudinal direction towards the center, thus forming numerous ridges on the wall of the matrix along the longitudinal direction. The ridged matrix was then chemically cross-linked with formaldehyde vapor at the humidity of 90–95% for 3–6 hours to stabilize the ridges and to control their in vivo stability. The cross-linked matrix was rinsed in water and air or freeze-dried. The ridges on the wall provide flexibility in the implant device, thus rendering it kink resistant.

An example of the implant device described above is shown in FIG. 1. The implant device 10 includes a tubular matrix 12. The tubular matrix has a diameter of d and a wall of a homogeneous thickness t. On the wall, there are a plurality of ridges 15.

EXAMPLE 4

Implant Device with a Micro Guiding System

The implant device of this invention optionally includes a micro guiding system which can be prepared by one of the following three methods:

i). Micro-tubes

The method of fabricating micro-tubes is similar to the method of fabricating a tubular implant device described in Example 3 except that the diameter of the mandrel used to fabricate the micro-tube is about 0.3–0.6 mm. The micro-tubes are also made kink resistant by the method described in Example 3.

The micro-tubes are inserted into the implant device prepared in Example 3, forming a micro guiding system which is defined by the walls of the micro-tubes.

An example of the implant device described above is shown in FIG. 2. The implant device 20 includes a tubular matrix 22 of a diameter of d22. The wall of the matrix 22 has a homogenous thickness t1 and a plurality of ridges 25. Within the tubular matrix, there are a number of microtubes 27 extending from one end to the other end of the matrix. Each microtube has a diameter of d27 and a wall of a homogenous thickness t2. On the wall of each microtube there are a plurality of ridges 28.

ii). Filaments

An aliquot of the purified collagen fibers is weighed and dispersed in a 0.07 M lactic acid solution. The dispersion is then loaded into a syringe and fixed onto a syringe pump extrusion system. The wet filaments are extruded into a 0.3% $NH_4OH$ coacervation solution and then into isopropanol. They are then removed from the isopropanol bath, air-dried, cross-linked with formaldehyde vapor, rinsed in water, and air-dried.

The filaments are inserted into the implant device prepared in Example 3, forming a micro guiding system which was defined by the inter-filamentary space.

An example of the implant device described above is shown in FIG. 3. The implant device 30 includes a tubular matrix 32, which has a wall of a homogenous thickness t. On the wall there are a plurality of ridges 35. Within the tubular matrix, there are a plurality of filaments 37. These filaments are parallel and extending from one end to the other end of the matrix.

iii). Porous Matrix with Channels

An aliquot of collagen fibers prepared in Example 1 is weighed and dispersed in 0.001 M NaOH solution, homogenized with a Silverson Homogenizer (East Longmeadow, Mass.), filtered with a stainless steel mesh filter (30 mesh), and neutralized to pH 7 with a 0.01 M HCl solution. The dispersion has a collagen content of 0.7% (w/v). The dispersion is de-aerated by centrifugation to remove the air trapped in the dispersion and concentrated to have a 1.4% collagen content.

Aliquots of the dispersion are subsequently freeze dried at −10° C. for 24 hours and at 20° C. for 10 hours in a tubular mold of various diameters ranging from 1–10 mm in the presence of fine pins of a diameter of 0.2 mm, fixed along the longitudinal direction of the tubular mold. The freeze-dried porous sponge matrix after removing the pins has parallel channels along the longitudinal direction of the porous matrix. The matrix is then cross-linked with vapor formaldehyde to stabilize the matrix and to control the in vivo stability.

The porous matrix is inserted into the implant device prepared in Example 3, forming a micro guiding system which is defined by the channels in the porous matrix.

An example of the implant device described above is shown in FIG. 4. The implant device 40 includes a tubular matrix 42 and a number of porous cylindrical matrices 46 within the matrix. The wall of the matrix, 42, is of a homogenous thickness t and has a plurality of ridges 44. Within each porous cylindrical matrix 46 there are a number of passages extending from one end to the other end of the matrix.

EXAMPLE 5

Incorporation of Bioactive Molecules bFGF, a net positively charged protein, is a potent mitogenic polypeptide that modulates cell proliferation and differentiation and promotes wound healing and angiogenesis. See Thompson et al. *Biochemistry*, 1994, 33; 3831–3840. It can be incorporated into a tubular implant device by first incorporating heparin into the implant device and then binding bFGF to the heparin.

Heparin, a negatively charged polysaccharide, has a high affinity to bFGF and can stabilize bFGF. A collagen-heparin composite is first prepared via physical and mechanical interaction by the following method: Collagen fibers are first swollen in an aqueous medium at pH below 4 or above 10. Heparin is then added into the swollen collagen fibers and subsequently diffused into the fiber domain. By adjusting the pH of the mixture to the isoelectric point of collagen (e.g., pH 4.5–5.0), the swollen collagen fibers coacervate and thereby entrap the heparin. An aliquot of the collagen-heparin dispersion is extruded into filaments by the method described in Example 4. The collagen-heparin filaments are air-dried and lightly cross-linked with glutaraldehyde (0.025%, pH 7.4) at room temperature for 8 hours to stabilize the collagen-heparin matrix.

Heparin-collagen composite can be fabricated into a tubular matrix by the method described in Example 3. The matrix is cross-linked with formaldehyde vapor to stabilize the collagen-heparin matrix by preserving the porous structure of the matrix.

The amount of incorporated heparin in the collagen-heparin composite is determined by sulfur analysis (Galbraith Laboratories, Knoxville, Tenn.) using pure heparin sodium as a baseline for the sulfur content. It is found that, in general, approximately 85–90% of the theoretical amount of heparin is incorporated into the composite tubular matrix.

The stability of the heparin in the tubular matrix is determined by the following method: The collagen-heparin tubular matrix is placed in a silastic tubing and subjected to a continuous flow (300 mL/min) condition by circulating a physiological saline solution at room temperature in the presence of thymol (a bacteriostatic agent). Samples are removed after 1, 3, and 7 days and assayed for the heparin activity. The heparin activity is determined with a factor Xa assay kit (Sigma, St. Louis, Mo.). The results of this study indicate that about 40–50% heparin activity remained at the end of 7 days.

In the tubular collagen-heparin matrix there are two pools of heparin. One pool of heparin is mechanically entangled with and/or entrapped in the collagen fibers, and the other pool of heparin is strongly associated with the collagen matrix (e.g., covalently bonded with the collagen matrix or strongly entrapped within the crosslinked collagen mesh matrix). The pool of heparin that is mechanically associated with the collagen matrix slowly diffused out from the matrix in 24 hours, while the strongly associated heparin molecules remained in the matrix for a longer period of time. Approximately 40–50% of the total heparin molecules are strongly associated with the collagen matrix.

bFGF is bound to a dried collagen-heparin tubular, filamental, or porous matrix via electrostatic interactions by the following method: A matrix is incubated in a bFGF solution containing 20 mg/mL in 0.01 M phosphate buffer (0.5 mg/mL collagen-heparin composite) for 24 hours at room temperature with agitation. The amount of bFGF incorporation into the collagen-heparin matrix is estimated by determining the residual amount of bFGF remaining in the solution using the Coomassie plus blue protein assay. (Bradford, M. M. 1976. A rapid and sensitive method for the quantitation of microgram quantities of proteins utilizing the principle of protein-dye binding. Anal. Biochem. 72:248). It is observed that the amount of incorporated bFGF increased with the increase of heparin amount in the collagen-heparin composite.

The stability of bFGF in collagen-heparin-bFGF matrix is evaluated by the following method: The matrix is incubated at 37° C. in a pH 7.4 PBS (0.01 M, 0.5 mg matrix/mL) under constant agitation for 24, 48, and 120 hours. The solution is assayed for bFGF that dissociated from the composite by the Coomassie plus blue protein assay. Since collagen is in the insoluble form and at 37° C. it tends to coacervate rather than to dissociate, the amount of collagen which dissociates into the solution is negligible. The results show that 50–80% of the bFGF remained associated with the collagen-based matrices.

EXAMPLE 6

Incorporation of Cells into the Implant i. Schwann Cells

Schwann cells are isolated from adult rats using the method of Scarpini, et al., *Exp. Neurology*, 102:167–176, 1988. The cells are seeded into the implant at a concentration of $2 \times 10^6$ cells/cm$^2$. The tubular implant is closed at one end with suture prior to seeding the cells. The cells are then pressure sodded through a syringe needle and the other end sutured. The seeded implant is placed in a culture plate filled with fresh mitogenic media [Dulbeccos Modified Eagles Medium (DMEM)] with fetal calf serum, 2 mm forskolin and 10 mg/ml pituitary extract) for two to three weeks. The cell seeded implant is trimmed at each end and ready for in vivo implantation for nerve repair.

ii. Epithelial Cells

Human transitional epithelial cells (HT-1367) from American Type Culture Collection (ATCC) are used. The epithelial cells are cultured in Modified Eagles Medium (MEM) in Earl's BSS with non-essential amino acids. The cells are grown to confluence, and then stripped for subculturing using 0.25% trypsin and 0.02% ethylenediaminetetraacidic acid (EDTA). The cells are washed and resuspended at a concentration of $1 \times 10^7$ cells/ml of medium. These cells are seeded into presoaked tubular implant similar to the Schwann cells described in (i). After 2–3 weeks of culture, the implant is ready for in vivo implantation.

iii. Endothelial Cells

Rat endothelial cells are isolated from fat pads of retired breeder Sprague Dawley rats according to the method of Jarrell, et al., *Surgery*, 100:392–399, 1986. The cells are seeded at $1-3 \times 10^6$ cells/cm$^2$. Endothelial cells are filtered onto the lumenal surface by introducing the cell suspension into the lumen after capping the ends with Luer lock connectors, and then forcing the medium through the sides of the tube under 5 PSI pressure to deposit the cells onto the surface. The endothelial cell seeded matrix is ready for in vivo implantation.

EXAMPLE 7

Physical and Mechanical Characterization of the Implant Device

Physical and mechanical characteristics of an implant device of this invention are assessed in the following aspects:

i). Kink Resistance

Kink resistance, defined as the maximum angle of bending without kinking, is determined by placing an implant device on a platform and bending it as far as possible without the observation of kinking. The angle of bending is monitored with an angle measurement device. The results show a high kink resistant angle of up to 140 degrees.

ii). Hydrothermal Shrinkage Temperature

The hydrothermal shrinkage temperature is defined as the onset temperature at which the length of the sample starts to change.

An implant device of this invention is first fixed in an apparatus designed for the hydrothermal shrinkage temperature measurement. The sample was then equilibrated with phosphate buffered saline (PBS) at 35° C. for 20 minutes. The temperature of the equilibrated solution was then raised at a rate of 1° C./minute. The length of the sample was measured as a function of the temperature. The hydrothermal shrinkage temperature is defined as the onset temperature when the length started to change. The average hydrothermal shrinkage temperature is $56 \pm 1.5°$ C.

iii). In Vivo Stability Evaluation

The in vivo stability and resorbability of an implant device was determined by the following experiment: Collagen membrane materials of different hydrothermal shrinkage temperatures were implanted subcutaneously in rats. At predetermined time points the rats were sacrificed and the amount of residual collagen implants remaining was determined by histological means. The total resorption time of each membrane material was obtained by extrapolation of the residual amount of collagen as a function of time to a value where the area occupied by the residual implant collagen was less than 2%. The total resorption time and the hydrothermal shrinkage temperature of the membranes is a linear relationship.

Based on the relationship, a matrix material can be selected for certain in vivo stability, based on its hydrothermal shrinkage temperature. For example, if the desired in vivo stability is 3–6 months, a hydrothermal shrinkage temperature of the collagen nerve repair implant in the range 50–55° C. will be suitable.

iv). Apparent Density

The density of a dry tubular implant device was determined by a gravimetric method. The implant device was first dried under vacuum for 24 hours and the dry weight was recorded. The dimensions (length, thickness and diameter) of the implant were then measured with a micrometer and a ruler. Thus, the density was a measure as the amount of collagen per unit volume of implant and was represented in g/cm$^3$.

The density of a micro-guiding system was determined also by the gravimetric method. The weight and dimension of each guiding system was determined and density of various guiding systems were then calculated. The average density of the implant device matrices is 0.65 g/cm³.

v). Mechanical Strength

Suture pullout strength was determined as follows: The implant was cut to a size of 20 mm×5 mm and soaked in pH 7.4 PBS at 25° C. for about 5 minutes. A suture (3-0 silk black braided, taper SH-1, Ethicon, Somerville, N.J.) was placed through the 20 mm membrane side at approximately 3 mm from the edge. The suture was tied into a knot, secured to the hook adapter of the tensile tester, clamped, and pulled at a speed 1.0 in/minute until the suture was pulled out. The suture pull out strength is 160±35 g.

vi). Permeability

The permeability was determined by tying one end of the tubular implant with suture, filling it with a fixed volume of carbonic anhydrase (MW 29,000) in PBS solution and tying the other end with suture. The sample was placed in a chamber filled with 5 mL PBS, and was allowed to equilibrate in the PBS for 24±4 hours at 22±3° C. with agitation. An aliquot of the solution in the chamber was assayed for the concentration of the probe molecule by the Bradford method described above. The matrix of the implant was permeable to molecules with a molecular weight of 29,000.

EXAMPLE 8

Use of an Implant Device in Median Nerve Repair

A median nerve of a male monkey is transected 2 cm above the wrist. The proximal and distal nerve stumps of the nerve are sutured into a tubular implant about 2 mm from the edge of the implant device of the present invention with a single 10-0 suture at each stump. The assessments of return of motor and sensory nerve function are performed under general anesthesia by standard electrophysiological means as described in Li et al. *Biotechnology and Polymers* by Gebelein (ed.), p 281–293, Plenum, N.Y., 1991.

EXAMPLE 9

Use of an Implant Device in Cavernosal Nerve Repair

Male patients with adenocarcinoma of the prostate underwent a radical prostatectomy procedure. One of the major side effects of the surgery is the damage to the cavernosal nerve, which results in impotency.

The implant device of this invention was used to repair the cavernosal nerve during radical prostatectomy by two different surgical methods.

i). Repair of Cavernosal Nerve with Nerve Guide Alone:

When unilateral resection of the cavernosal (either left or right) nerve is performed during a radical prostatectomy procedure, the cavernosal nerve stumps are sutured into an implant device described in example 5 of the present invention (3 mm ID and 5 cm length) by the method described above in median nerve repair. Two tubular implants are used to repair the nerves when both the left and right cavernosal nerves were resected.

ii). Repair of Cavernosal Nerve with a Nerve Autograft and an Implant Device:

An autograft of a sural nerve was harvested from the patient. For unilateral cavernosal nerve repair, an appropriate length of the nerve graft and the cavernosal nerve stumps sutured to the ends of two tubular implants (3 mm ID and 5 cm length) with a single 10-0 suture. The sural nerve-nerve guide composite is then placed into the cavernosal nerve repair site. For bilateral nerve repair, the procedure on the contralateral side (either left or right) is repeated as above. This procedure is performed either after completion of the radical prostatectomy by a perineal approach or during the prostatectomy procedure by a retropubic approach. The completed procedure left a gap of 1–5 mm between the cavernosal nerve stumps and the nerve autograft. The return of erectile function is assessed by standard patient questionnaire and instrumentation to measure the erectile function during sleep (Rigiscan, UroHealth Systems, Inc. Laguna Niguel, Calif.).

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. An implant device comprising a tubular matrix made of a biocompatible and bioresorbable biopolymeric material, the tubular matrix having a first end and a second end; a wall of uniform thickness and disposed such that it forms ridges; and a channel which is defined by the wall and extends from the first end to the second end of the tubular matrix; wherein the ridges form undulations in the surface of the tubular matrix.

2. The implant device of claim 1, wherein the tubular matrix has an internal diameter of 0.1 mm to 10 mm, a length of 0.3 cm to 15 cm, and a thickness of 0.02 mm to 1 mm.

3. The implant device of claim 1, wherein the tubular matrix has a molecular weight cutoff of 500,000.

4. The implant device of claim 3, wherein the tubular matrix has an internal diameter of 0.1 mm to 10 mm, a length of 0.3 cm to 15 cm, and a thickness of 0.02 mm to 1 mm.

5. The implant device of claim 1, wherein the biocompatible and bioresorbable biopolymeric material is collagen-based.

6. The implant device of claim 5, wherein the tubular matrix has an internal diameter of 0.1 mm to 10 mm, a length of 0.3 cm to 15 cm, and a thickness of 0.02 mm to 1 mm.

7. The implant device of claim 5, wherein the tubular matrix has a molecular weight cutoff of 500,000.

8. The implant device of claim 7, wherein the tubular matrix has an internal diameter of 0.1 mm to 10 mm, a length of 0.3 cm to 15 cm, and a thickness of 0.02 mm to 1 mm.

9. The implant device of claim 7, wherein the tubular matrix has a molecular weight cutoff of 100,000.

10. The implant device of claim 9, wherein the tubular matrix has an internal diameter of 0.1 mm to 10 mm, a length of 0.3 cm to 15 cm, and a thickness of 0.02 mm to 1 mm.

11. The implant device of claim 1, further comprising a plurality of cylindrical matrices made of a biocompatible and bioresorbable biopolymeric material, wherein the cylindrical matrices are disposed inside the channel and parallel to the longitudinal axis of the tubular matrix; each cylindrical matrix has two ends, a wall of a uniform thickness and disposed such that it forms ridges, and a passage which is defined by its wall and extends along the cylindrical matrix; and the passage of at least one cylindrical matrix is of suitable dimension for receiving a nerve to be repaired.

12. The implant device of claim 11, wherein the tubular matrix has an internal diameter of 0.1 mm to 10 mm, a length of 0.3 cm to 15 cm, and a thickness of 0.02 mm to 1 mm.

13. The implant device of claim 11, wherein the tubular matrix has a molecular weight cutoff of 500,000.

14. The implant device of claim 13, wherein the tubular matrix has an internal diameter of 0.1 mm to 10 mm, a length of 0.3 cm to 15 cm, and a thickness of 0.02 mm to 1 mm; and each cylindrical matrix has an internal diameter of 0.1 mm to 2 mm, a length of 0.3 cm to 15 cm, and a thickness of 0.02 mm to 1 mm.

15. The implant device of claim 11, wherein the biocompatible and bioresorbable biopolymeric material is collagen-based.

16. The implant of claim 15, wherein the tubular matrix has an internal diameter of 0.1 mm to 10 mm, a length of 0.3 cm to 15 cm, and a thickness of 0.02 mm to 1 mm; and each cylindrical matrix has an internal diameter of 0.1 mm to 2 mm, a length of 0.3 cm to 15 cm, and a thickness of 0.02 mm to 0.5 mm.

17. The implant device of claim 15, wherein the tubular matrix has a molecular weight cutoff of 500,000.

18. The implant device of claim 17, wherein the tubular matrix has an internal diameter of 0.1 mm to 10 mm, a length of 0.3 cm to 15 cm, and a thickness of 0.02 mm to 1 mm; and each cylindrical matrix has an internal diameter of 0.1 mm to 2 mm, a length of 0.3 cm to 15 cm, and a thickness of 0.02 mm to 0.5 mm.

19. The implant device of claim 17, wherein the tubular matrix has a molecular weight cutoff of 100,000.

20. The implant device of claim 19, wherein the tubular matrix has an internal diameter of 0.1 mm to 10 mm, a length of 0.3 cm to 15 cm, and a thickness of 0.02 mm to 1 mm; and each cylindrical matrix has an internal diameter of 0.1 mm to 2 mm, a length of 0.3 cm to 15 cm, and a thickness of 0.02 mm to 0.5 mm.

21. The implant device of claim 1, further comprising a plurality of filaments made of a biocompatible and bioresorbable biopolymeric material, wherein the filaments are disposed inside the channel and parallel to the longitudinal axis of the tubular matrix, thereby forming inter-filamental spaces; and at least one inter-filamental space is of suitable dimension for receiving a nerve to be repaired.

22. The implant device of claim 21, wherein the tubular matrix has an internal diameter of 0.1 mm to 10 mm, a length of 0.3 cm to 15 cm, and a thickness of 0.02 mm to 1 mm; and each filament has a diameter of 0.03 mm to 0.5 mm and a length of 0.3 cm to 15 cm.

23. The implant device of claim 21, wherein the tubular matrix has a molecular weight cutoff of 500,000.

24. The implant device of claim 23, wherein the tubular matrix has an internal diameter of 0.1 mm to 10 mm, a length of 0.3 cm to 15 cm, and a thickness of 0.02 mm to 1 mm; and each filament has a diameter of 0.03 mm to 0.5 mm and a length of 0.3 cm to 15 cm.

25. The implant device of claim 21, wherein the biocompatible and bioresorbable biopolymeric material is collagen-based.

26. The implant device of claim 25, wherein the tubular matrix has an internal diameter of 0.1 mm to 10 mm, a length of 0.3 cm to 15 cm, and a thickness of 0.02 mm to 1 mm; and each filament has a diameter of 0.03 mm to 0.5 mm and a length of 0.3 cm to 15 cm.

27. The implant device of claim 25, wherein the tubular matrix has a molecular weight cutoff of 500,000.

28. The implant device of claim 27, wherein the tubular matrix has an internal diameter of 0.1 mm to 10 mm, a length of 0.3 cm to 15 cm, and a thickness of 0.02 mm to 1 mm; and each filament has a diameter of 0.03 mm to 0.5 mm and a length of 0.3 cm to 15 cm.

29. The implant device of claim 27, wherein the tubular matrix has a molecular weight cutoff of 100,000.

30. The implant device of claim 29, wherein the tubular matrix has an internal diameter of 0.1 mm to 10 mm, a length of 0.3 cm to 15 cm, and a thickness of 0.02 mm to 1 mm; and each filament has a diameter of 0.03 mm to 0.5 mm and a length of 0.3 cm to 15 cm.

31. The implant device of claim 1, further comprising one or more porous cylindrical matrices made of a biocompatible and bioresorbable biopolymeric material, wherein the porous cylindrical matrices are disposed inside the channel and parallel to the longitudinal axis of the tubular matrix; and each cylindrical matrix has two ends and at least one passage parallel to its longitudinal axis, extending along the porous cylindrical matrix, and is of suitable dimension for receiving a nerve to be repaired.

32. The implant device of claim 31, wherein the tubular matrix has an internal diameter of 0.1 mm to 10 mm, a length of 0.3 cm to 15 cm, and a thickness of 0.02 mm to 1 mm; each porous cylindrical matrix has a diameter of 0.1 mm to 10 mm and a length of 0.3 cm to 15 cm; and each passage of each porous cylindrical matrix has a diameter of 0.1 mm to 2 mm and a length of 0.3 cm to 15 cm.

33. The implant device of claim 31, wherein the tubular matrix has a molecular weight cutoff of 500,000.

34. The implant device of claim 33, wherein the tubular matrix has an internal diameter of 0.1 mm to 10 mm, a length of 0.3 cm to 15 cm, and a thickness of 0.02 mm to 1 mm; each porous cylindrical matrix has a diameter of 0.1 mm to 10 mm and a length of 0.3 cm to 15 cm; and each passage of each porous cylindrical matrix has a diameter of 0.1 mm to 2 mm and a length of 0.3 cm to 15 cm.

35. The implant device of claim 31, wherein the biocompatible and bioresorbable biopolymeric material is collagen-based.

36. The implant device of claim 35, wherein the tubular matrix has an internal diameter of 0.1 mm to 10 mm, a length of 0.3 cm to 15 cm, and a thickness of 0.02 mm to 1 mm; each porous cylindrical matrix has a diameter of 0.1 mm to 10 mm and a length of 0.3 cm to 15 cm; and each passage of each porous cylindrical matrix has a diameter of 0.1 mm to 2 mm and a length of 0.3 cm to 15 cm.

37. The implant device of claim 35, wherein the tubular matrix has a molecular weight cutoff of 500,000.

38. The implant device of claim 37, wherein the tubular matrix has an internal diameter of 0.1 mm to 10 mm, a length of 0.3 cm to 15 cm, and a thickness of 0.02 mm to 1 mm; each porous cylindrical matrix has a diameter of 0.1 mm to 10 mm and a length of 0.3 cm to 15 cm; and each passage of each porous cylindrical matrix has a diameter of 0.1 mm to 2 mm and a length of 0.3 cm to 15 cm.

39. The implant device of claim 37, wherein the tubular matrix has a molecular weight cutoff of 100,000.

40. The implant device of claim 39, wherein the tubular matrix has an internal diameter of 0.1 mm to 10 mm, a length of 0.3 cm to 15 cm, and a thickness of 0.02 mm to 1 mm; each porous cylindrical matrix has a diameter of 0.1 mm to 10 mm and a length of 0.3 cm to 15 cm; and each passage of the porous cylindrical matrices has a diameter of 0.1 mm to 2 mm and a length of 0.3 cm to 15 cm.

41. The implant device of claim 1, further comprising bioactive molecules.

42. The implant device of claim 41, wherein the bioactive molecules are growth factors.

43. The implant device of claim 42, wherein the growth factors are acidic and basic fibroblast growth factors, insulin-like growth factors, epidermal growth factors, bone morphogenetic proteins, nerve growth factors, neurotrophic factors, TGF-b, platelet derived growth factors, or vascular endothelial cell growth factor.

44. The implant device of claim 42, wherein the growth factors promote cell adhesion, growth, and differentiation.

45. The implant device of claim 41, wherein the bioactive molecules are bioadhesive molecules.

46. The implant device of claim 45, whereas the bioadhesive molecules are laminins, fibronectins, adhesive glycoproteins, fibrin, glycosaminoglycans, or cell adhesive collagens.

47. The implant device of claim 1, wherein the device further comprises cells.

48. The implant device of claim 47, wherein the cells are Schwann cells.

49. The implant device of claim 47, wherein the cells are Sertoli's cells.

50. The implant device of claim 47, wherein the cells are epithelial cells.

51. The implant device of claim 47, wherein the cells are endothelial cells.

52. The implant device of claim 47, wherein the cells are stem cells.

53. A method of preparing a ridged tubular matrix, comprising:

fabricating a tubular matrix having a wall of uniform thickness comprising biopolymeric fibers;

drying the tubular matrix;

humidifying the tubular matrix;

pressing the tubular matrix along its longitudinal axis to cause formation of ridges on the wall thereof; and crosslinking the biopolymeric fibers to obtain a ridged tubular matrix;

wherein the ridges form undulations in the surface of the tubular matrix.

54. The method of claim 53, wherein the biopolymeric fibers are prepared from collagen.

* * * * *